US005733775A

United States Patent [19]

Puchegger et al.

[11] Patent Number: 5,733,775

[45] Date of Patent: Mar. 31, 1998

[54] TEMPERATURE CONTROL DEVICE

[75] Inventors: Karl Puchegger, Salzburg; Andreas Erlbacher, Abtenau; Josef Atzler, Hallein, all of Austria

[73] Assignee: SLT Labinstruments Gesellschaft m.b.H., Grödig/Salzburg, Austria

[21] Appl. No.: 606,944

[22] Filed: Feb. 26, 1996

[30] Foreign Application Priority Data

Feb. 27, 1995 [AT] Austria .................................... 99/95 U

[51] Int. Cl.$^6$ .................................................... C12M 3/00

[52] U.S. Cl. .................................... 435/286.1; 435/286.2; 366/145; 366/147; 366/204

[58] Field of Search .............................. 435/286.1, 286.7, 435/287.2; 366/145, 147, 204

[56] References Cited

U.S. PATENT DOCUMENTS 5,466,603 11/1995 Meehan et al. ....................... 435/285.1

FOREIGN PATENT DOCUMENTS

WO 89/07763 8/1989 WIPO .......................... G01N 33/543

WO 89/06369 5/1991 WIPO ............................... B01L 7/00

*Primary Examiner*—David A. Redding

*Attorney, Agent, or Firm*—Wenderoth, Lind & Ponack

[57] ABSTRACT

A temperature control device controls the temperature of the contents of a pan-shaped specimen container, in particular for the temperature control of specimen strips by hybridization assays. The specimen container can be set sealingly into a movably supported housing for a water bath.

9 Claims, 5 Drawing Sheets

TEMPERATURE CONTROL DEVICE

BACKGROUND OF THE INVENTION

The invention relates to an apparatus to be used for control of the temperature of the contents of a pan-shaped specimen container, in particular for the temperature control of specimen strips for hybridization assays.

For hybridization assays a very precise temperature control of the specimen strips during part of their development is required. The specimen strips are disposed in individual chambers of a specimen carrier of a synthetic material. The synthetic specimen carrier is preferably a molded polystyrene part or a synthetic injection molded part. The individual chambers form reaction vessels for developing the specimen strips and the appropriate reagents are added sequentially or drawn off or poured off again. During the incubation time the liquid above and around the Specimen strips must be kept in motion.

SUMMARY OF THE INVENTION

It is the task of the invention to create a device of the above stated type which permits highly precise temperature control of the specimen strips.

The task according to the invention is solved with a movably supported housing for a water bath into which the specimen container can be set in a sealed manner.

The pan-shaped specimen container is disposable and must be changed by the user frequently, if necessary after each test. About the underside of the specimen container in the device according to the invention flows temperature-controlled water of the water bath. In the device according to the invention the pan-shaped specimen container and its contents are completely sealed against the water bath.

BRIEF DESCRIPTION OF THE DRAWINGS in the following an embodiment of the invention will be described in detail in conjunction with the attached drawings, wherein.

DETAILED DESCRIPTION OF THE INVENTION

Figure 1:
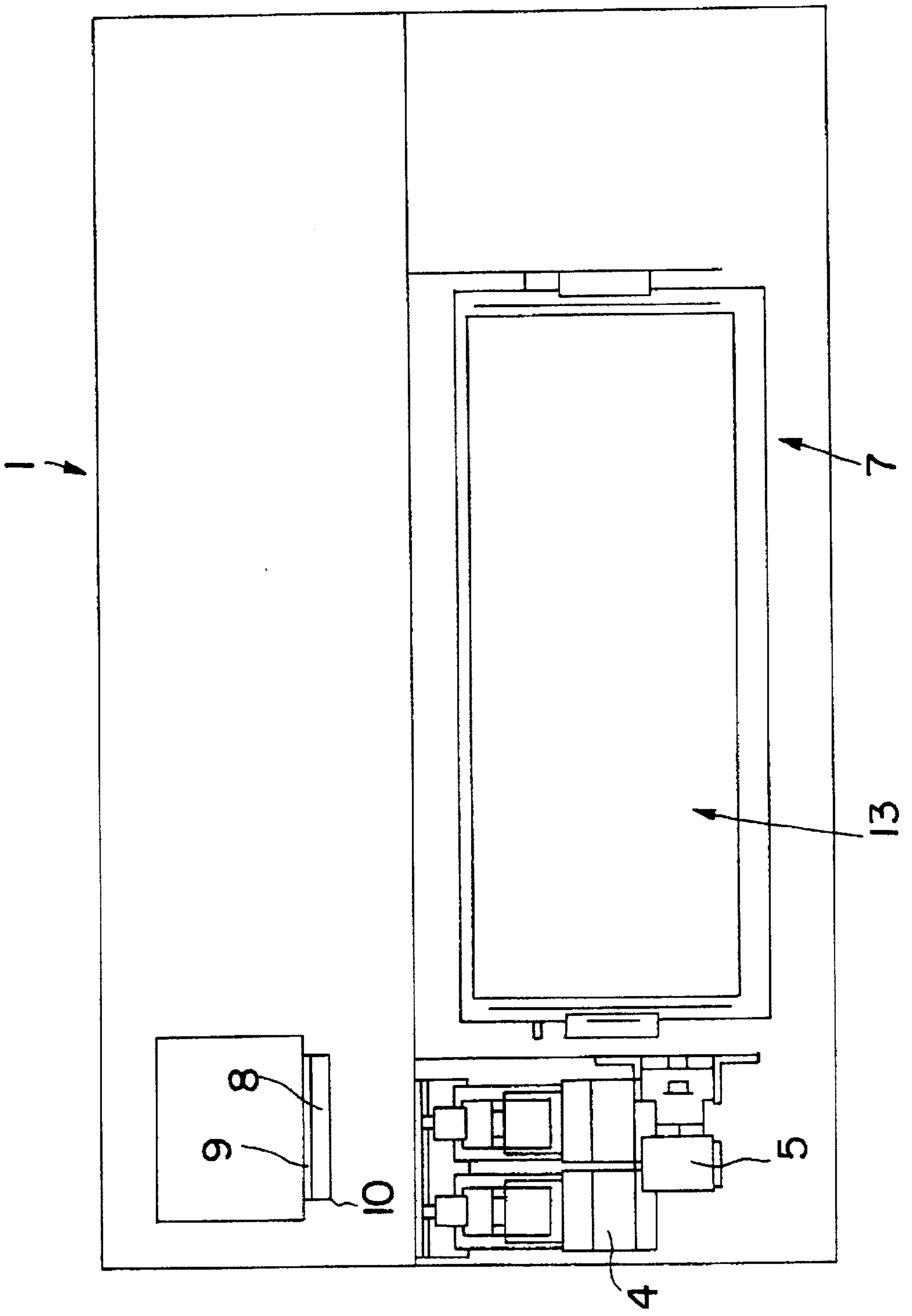
FIG. 1 is a top view of a device according to the invention.
Figure 2:
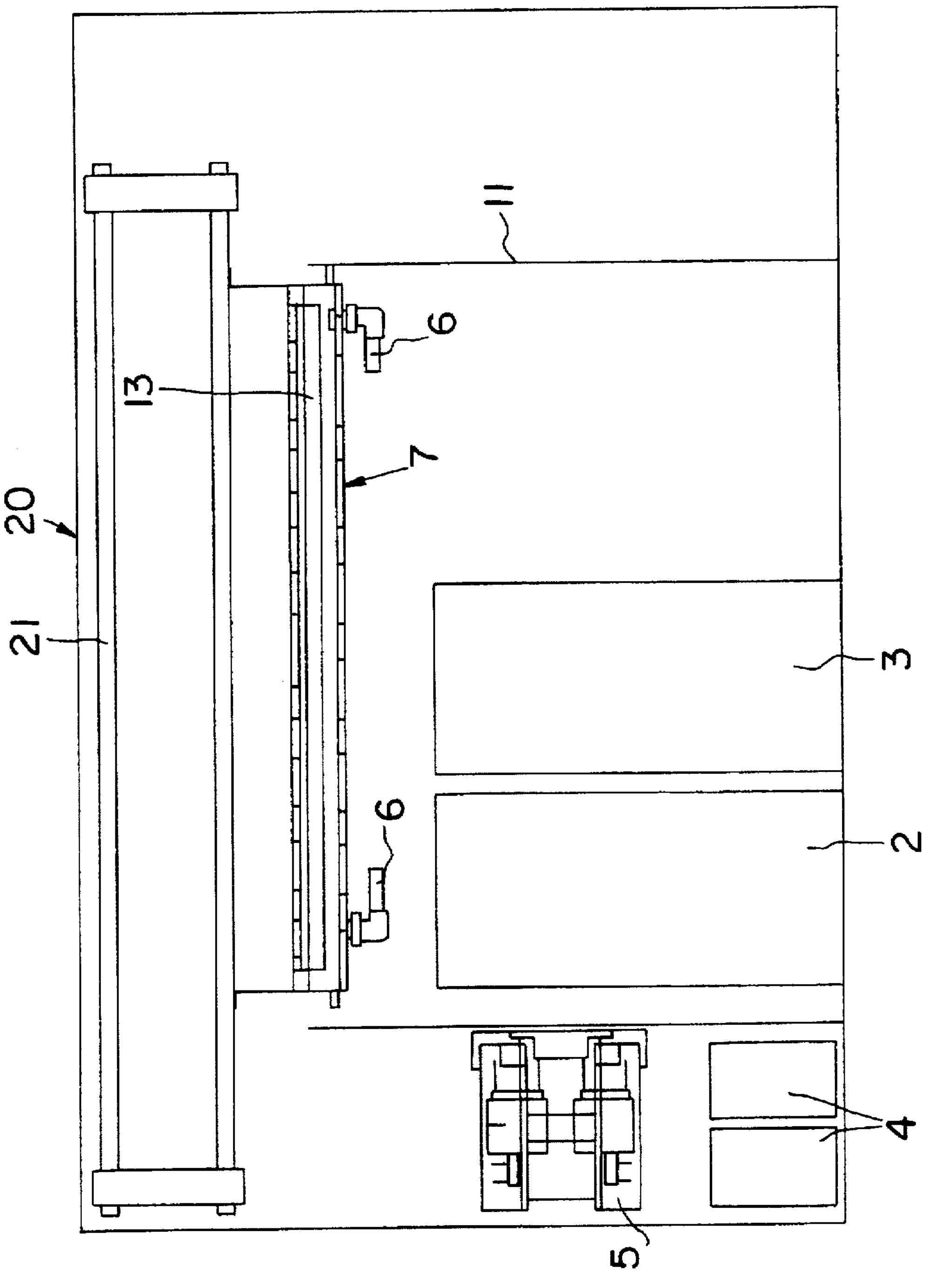
FIG. 2 is a front view of the device according to the invention.
Figure 3:
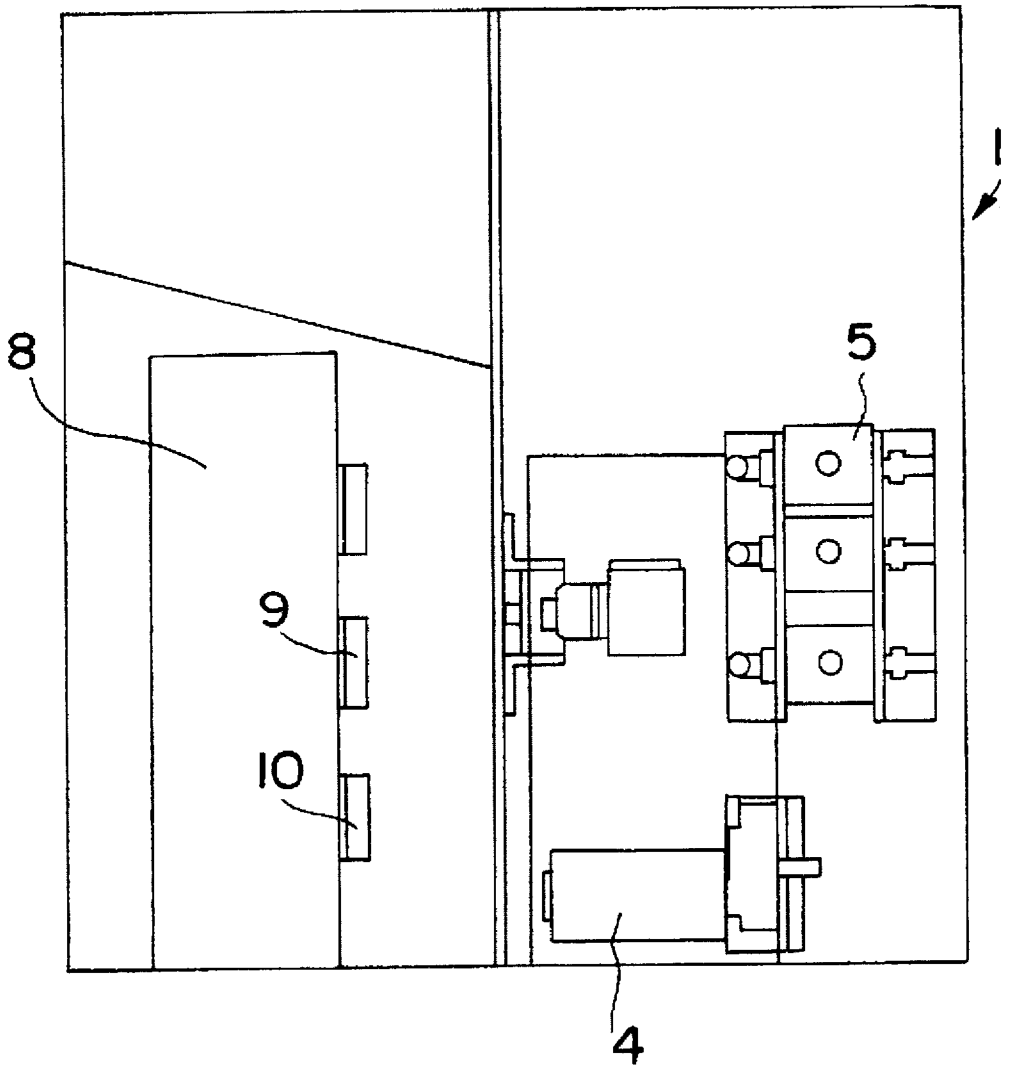
FIG. 3 is a side view of the device according to the invention.
Figure 4:
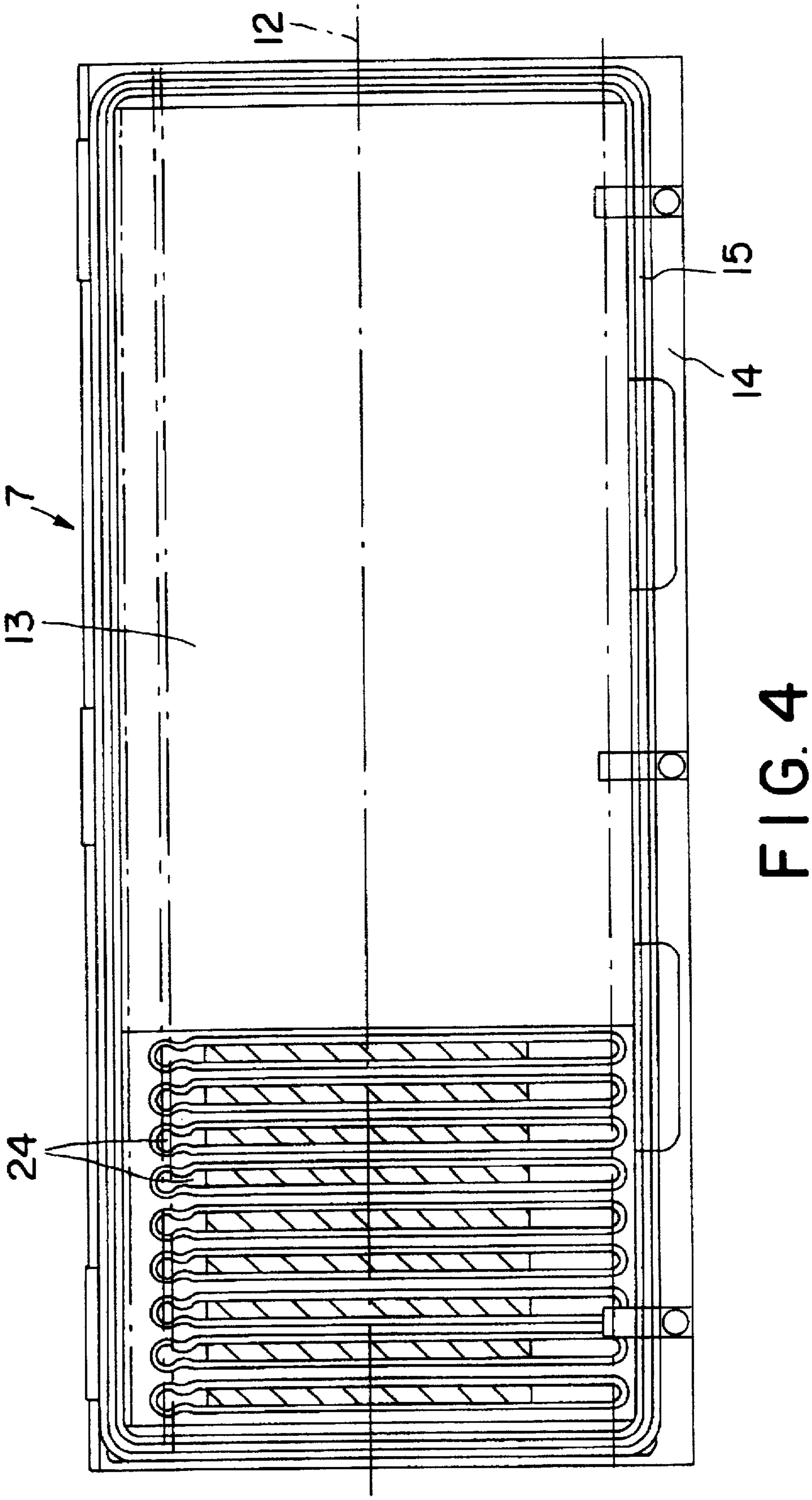
FIG. 4 is a top view of a housing for water bath.

The device according to the invention comprises a warm water container 2 and a cold water container 3 connected via pumps 4 and valves 5 with ports 6 of a pan-shaped housing 7. In the embodiment shown, water for cooling a water bath is cooled in a cooling unit 8 and/or heated by means of Peltier elements 9 and heat exchangers 10. It would, however, also be possible to generate warm water by means of resistance heating and to use tap water as the cooling water.

The pan-shaped housing 7 is movably supported in a frame 1 and preferably carries out a rocking motion about central transverse axis 12. Into each housing 7 can be placed a pan-shaped specimen container 13. The specimen container 13 comprises several pans 24 in each of which is disposed one specimen strip for a hybridization assay. The housing 7 is set into rocking motion via a (not shown) device, for example by means of an eccentric.

Figure 5:
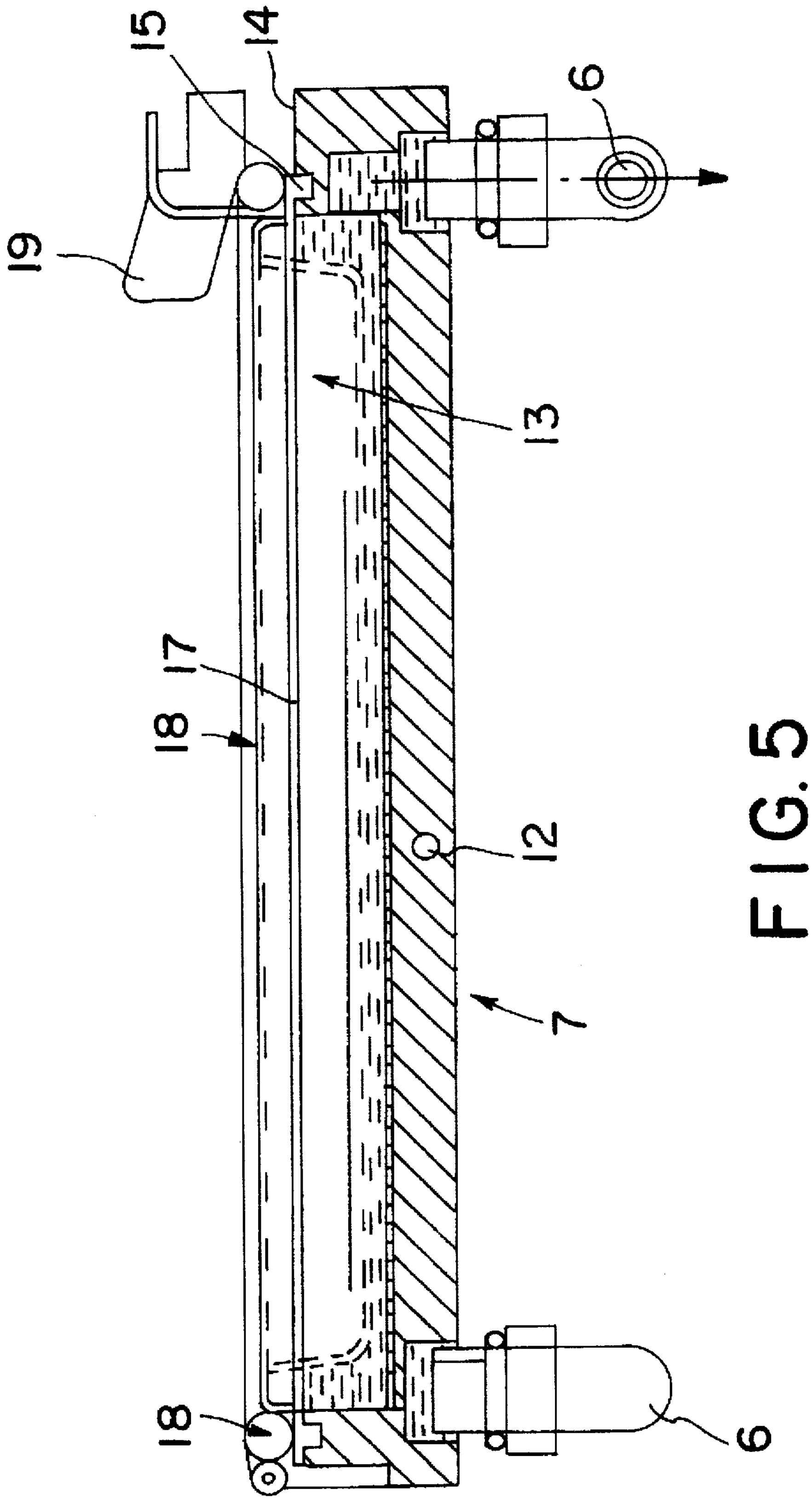
FIG. 5 is a side view of the housing for the water bath with a specimen container therein.

As is evident from FIG. 5, the housing 7 comprises an edge 14 into which is set a seal 15. From case to case, the specimen container 7 is provided with a cover and comprises a laterally projecting edge 17 which, after the specimen container 13 has been set into housing 7, rests on top of the seal 15. The seal 15 extends over the entire edge 14 of housing 7. Housing 7 is furthermore provided with a frame 18 and a clamping device 19. By means of the frame 18, the edge 17 of the specimen container 13 is pressed against the seal 15, thus forming a seal.

Above the housing 7 is provided a transporting device with rails 21 for transporting the reagents.

We claim:

1. An apparatus to be used for the control of the temperature of the contents of a pan-shaped specimen container, in particular for the temperature control of specimen strips for hybridization assays, said apparatus comprising:

a housing adapted to contain a water bath;

said housing being configured to sealingly receive the specimen container in the water bath; and said housing being mounted so as to be capable of motion.

2. An apparatus as claimed in claim 1, further comprising a frame, said housing being mounted on said frame for movement relative thereto.

3. An apparatus as claimed in claim 1, wherein said housing includes an edge having thereon an encompassing seal, and further comprising a frame disposed above said seal and operable to clamp a laterally projecting edge of the specimen container against said seal.

4. An apparatus as claimed in claim 1, wherein said housing includes ports for a water feed line and a water drain line.

5. An apparatus as claimed in claim 1, further comprising a drive for imparting to said housing a swaying motion.

6. An apparatus as claimed in claim 1, further comprising a transporting device for transporting reagents to said housing and for the removal of reagents therefrom.

7. An apparatus as claimed in claim 6, wherein said transporting device comprises rails which extend above said housing.

8. An apparatus device as claimed in claim 1, further comprising heat exchangers with Peltier elements and a cooling unit for temperature control of water for the water bath.

9. A device as claimed in claim 1, wherein said housing is mounted in a manner to enable rocking movement thereof about a central transverse axis thereof.

* * * * *